United States Patent [19]

Glamkowski et al.

[11] Patent Number: 5,260,452
[45] Date of Patent: Nov. 9, 1993

[54] 4- AND 6-CARBAMATES RELATED TO PHYSOSTIGMINE AND INTERMEDIATES FOR THE PREPARATION THEREOF

[75] Inventors: Edward J. Glamkowski, Warren; Barbara E. Kurys, Elmwood Park, both of N.J.

[73] Assignee: Hoechst-Roussel Pharmaceuticals Inc., Somerville, N.J.

[21] Appl. No.: 753,547

[22] Filed: Sep. 3, 1991

Related U.S. Application Data

[62] Division of Ser. No. 431,103, Nov. 3, 1989, Pat. No. 5,081,117.

[51] Int. Cl.⁵ .......................................... C07D 209/34
[52] U.S. Cl. .................................................. 548/486
[58] Field of Search ......................................... 548/486

[56] References Cited

PUBLICATIONS

Mori, Heterocycles 9(4) p. 328, 1978.
Beckett, Tetrahedron, 24(19) 6093 1968 Abstract.

*Primary Examiner*—Robert Gerstl
*Attorney, Agent, or Firm*—Elliott Korsen

[57] ABSTRACT

This invention relates to 4- and 6-carbamates related to physostigmine of the formula

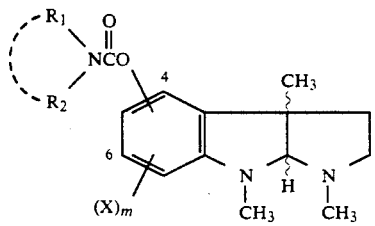

where $R_1$ is alkyl, cycloalkyl, bicycloalkyl, aryl or aryl-loweralkyl; $R_2$ is hydrogen or alkyl or the group $-NR_1R_2$ taken together forms a monocyclic or bicyclic ring of 5 to 12 carbons; m is 0, 1, or 2; each X is independently hydrogen, halogen, loweralkyl, nitro or amino; and the pharmaceutically acceptable acid addition salts thereof, and where applicable, the geometric and optical isomers and racemic mixtures thereof. This invention also relates to novel intermediates useful in the preparation of the 4- and 6-carbamates. The compounds of this invention display utility for alleviating various memory dysfunctions characterized by a decreased cholinergic function, such as Alzheimer's disease.

14 Claims, No Drawings

4- AND 6-CARBAMATES RELATED TO PHYSOSTIGMINE AND INTERMEDIATES FOR THE PREPARATION THEREOF

This is a division of application Ser. No. 431,103 filed Nov. 3, 1989 now U.S. Pat. No. 5,081,117.

This invention relates to 4- and 6-carbamates related to physostigmine of the formula

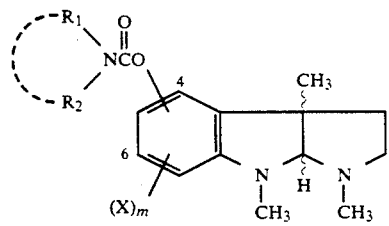

where $R_1$ is alkyl, cycloalkyl, bicycloalkyl, aryl or aryl-loweralkyl; $R_2$ is hydrogen or alkyl or the group $-NR_1R_2$ taken together forms a monocyclic or bicyclic ring of 5 to 12 carbons; m is 0, 1 or 2; each X is independently hydrogen, loweralkyl, nitro or amino; and the pharmaceutically acceptable acid addition salts thereof, and where applicable, the geometric and optical isomers and racemic mixtures thereof. The compounds of this invention display utility in the treatment of the cholinergic deficit found in Alzheimer's disease.

Subgeneric to the compounds of formula I above are compounds of formula II

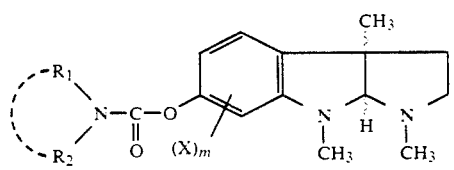

where $R_1$, $R_2$, X and m are as previously defined.

Also subgeneric to the compounds of formula I above are compounds of formula III below

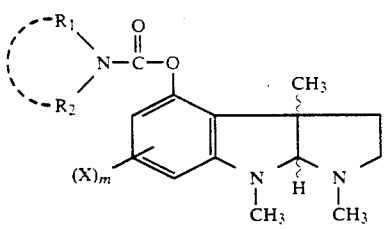

where $R_1$, $R_2$, X and m are as previously defined.

This invention also relates to compounds of formula IV

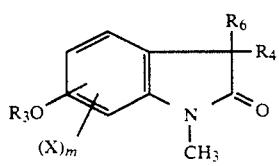

where $R_3$ is hydrogen or $R_4$ is hydrogen, cyanoalkyl or aminoalkyl, and $R_6$ is hydrogen or alkyl, which are useful as intermediates for the preparation of the target compounds of this invention.

Additionally, this invention relates to compounds of the formula

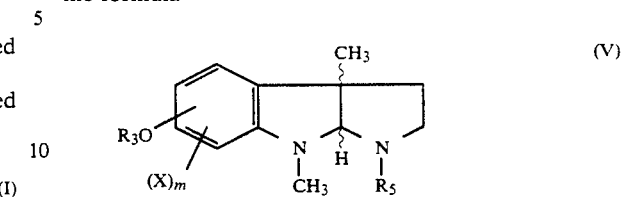

where $R_5$ is hydrogen or loweralkyl; and $R_3$, X and m are as previously defined, which are also useful as intermediates for the preparation of the target compounds of this invention.

Throughout the specification and appended claims, a given chemical formula or name shall encompass all geometric and optical isomers and racemic mixtures where such isomers and mixtures exist.

In the above definition, the term "lower" means the group it is describing contains from 1 to 6 carbon atoms. The term "alkyl" refers to a straight or branched chain hydrocarbon of 1 to 22 carbon atoms, containing no unsaturation, e.g., methyl, ethyl, propyl, isopropyl, 2-butyl, neopentyl, n-hexyl, etc.; the term "arylloweralkyl" refers to a monovalent substituent which consists of an "aryl" group, e.g., phenyl, o-tolyl, m-methoxyphenyl, etc., as defined by the formula

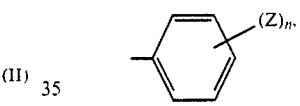

where Z is defined below, and n is an integer of 1 to 3, linked through a loweralkylene group having its free valence bond from a carbon of the loweralkylene group, and having a formula of

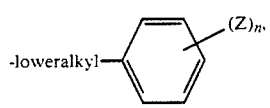

where Z is hydrogen, halogen, loweralkyl, loweralkoxy, trifluoromethyl, nitro and amino; the term "alkylene" refers to a bivalent radical of the lower branched or unbranched alkyl group it is derived from having valence bonds from two terminal carbons thereof, e.g., methylene ($-CH_2-$), ethylene ($-CH_2CH_2-$), propylene ($-CH_2CH_2CH_2-$), isopropylene ($CH(CH_3)(CH_2-)$), etc.; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; the term "halogen" refers to a member of the halogen family consisting of fluorine, chlorine, bromine and iodine; the term "cycloalkyl" refers to a monovalent substituent consisting of a saturated hydrocarbon possessing at least one carbocyclic ring of three to twelve carbon atoms, e.g., cyclopropyl, cyclobutyl, cyclopentyl, cyclohexyl, cycloheptyl, cyclooctyl, etc., having its free valence bond from a carbon of the carbocyclic ring. Said cycloalkyl group may be substituted with 1 or 2 loweralkyl groups, and it may also be substituted at one of the ring carbons so as to form a spiro compound each constitutent ring of which being a cycloalkyl of 3 to 8 carbon atoms; and the term "bicycloalkyl" shall mean a bicycloalkyl group having from 7 to 11 carbon atoms.

The compounds of this invention are prepared in the following manner. The substituents $R_1$, $R_2$, $R_3$, $R_4$, $R_5$, $R_6$, X and m are as defined above unless indicated otherwise.

In structural formulas depicting the compounds of this invention, wavy lines (~~~) signify that the two substituents are both either above or below the average plane of the three ring system. Because of conformational constraints, the two substituents at the 3a- and 8a-positions must be both above the average plane or both below the average plane. Where said substituents are both above the average plane of the three ring system, the configuration is referred to as 3aS-cis and where both substituents are below the average plane of the ring, the configuration is referred to as 3aR-cis. Throughout the specification and the appended claims, when the inventors intend to designate in a single formula (to save space) that the compound is 3aS-cis, or 3aR-cis, or a racemic mixture of the two, that formula will contain wavy lines as depicted below.

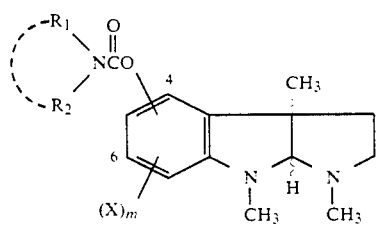

It is the intent of the present inventors to claim both of said cis isomers, namely, 3aS-cis and 3aR-cis for each compound name or structural formula. It is also the intent of the present inventors to claim all mixtures of the 3aS-cis and 3aR-cis isomers including the racemic mixture (1:1 ratio of 3aS-cis:3aR-cis).

The 6-hydroxyl precursor of the 6-carbamoyl series is synthesized as outlined below.

Starting with a compound of formula VI (where X is hydrogen, loweralkyl, halogen or nitro) and utilizing generally the synthetic scheme disclosed in Julian et al., J. Chem. Soc. 1935, 563-566 and 755-757, one can prepare compounds of the invention of the formula VI through XIV. Julian's synthesis involved compounds where the benzene ring of the bicyclic and tricyclic compounds had substituents attached at the 5-position while the novel compounds of this invention are attached at either the 4- or 6-position of the ring. The synthetic scheme is outlined below. For details of the optical resolution steps involved in the synthetic scheme, reference is made to the Julian article, pp. 755-757 and to Schonenberger et al., J. Med. Chem., 1986, Volume 29, 2268-2273; and Schonenberger et al., Helv. Chim. Acta., 1986, Volume 69, 283-287 and 1486-1497.

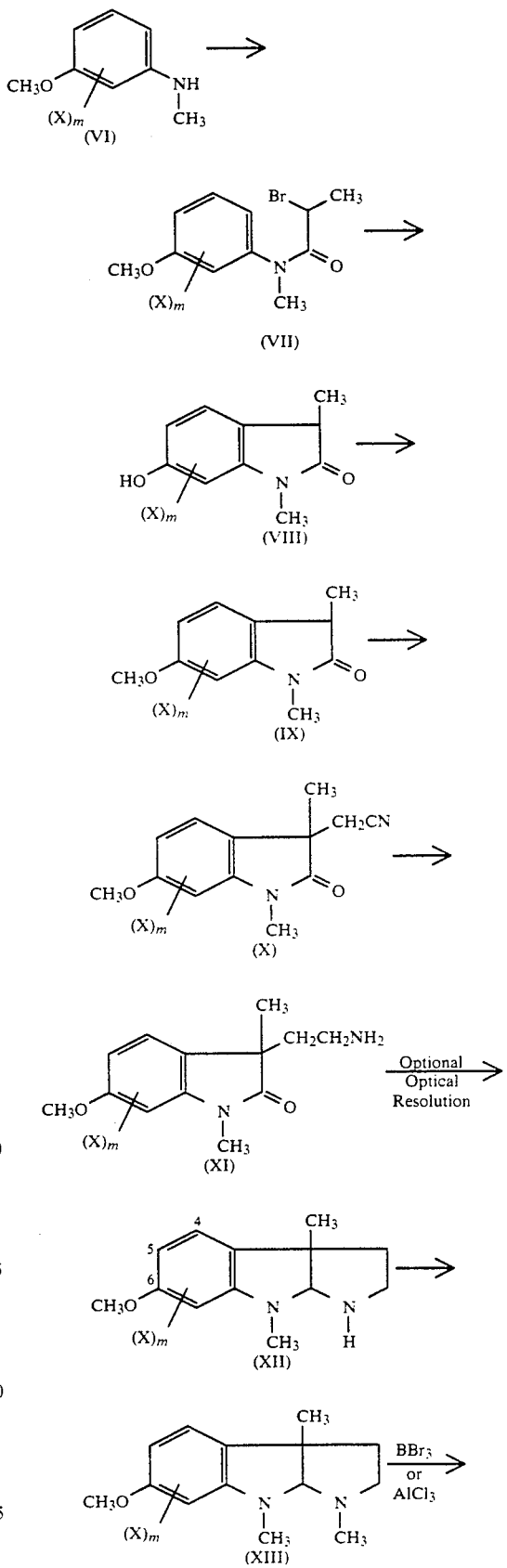

-continued

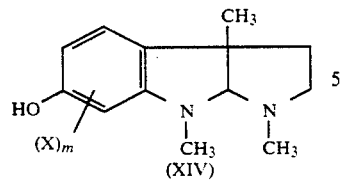

Compound XIV of the invention of the formula

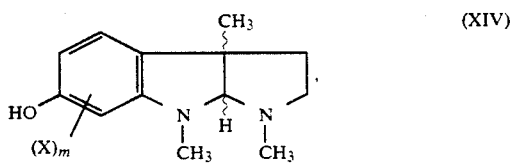

the 6-phenol precursor of the 6-carbamate, can be added to a suitable inert solvent, e.g., benzene, tetrahydrofuran, dichloromethane, etc., which has previously been degassed. Degassing helps avoid air oxidation. After stirring, 1,8-diazabicyclo[5.4.0]undec-7-ene (hereafter "DBU"), a bicyclic amidine catalyst is added. Subsequently, an isocyanate of the formula $R_1$—N=C=O, where $R_1$ is as previously defined, is added to afford compound II of the invention. This reaction typically takes place rapidly at room temperature over 0.5 to 2 hours.

In an alternative embodiment, to prepare the 6-carbamate of the invention where the group —$NR_1R_2$ taken together forms a bicyclic ring, Compound XIV can be reacted with 1,1'-carbonyldiimidazole of the formula

and thereafter adding a cyclic amine, for example 3-azabicyclo[3.2.2]nonane of the formula

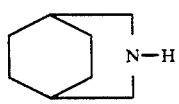

to the solution. The reaction between compound XIV and 1,1'-carbonyldiimidazole is typically conducted by preparing a degassed solution of compound XIV in a suitable inert solvent such as dichloromethane, tetrahydrofuran, etc., adding 1,1'-carbonyldiimidazole to the solution and stirring the solution at room temperature for 1 to 5 hours. The carbamation reaction is typically conducted by adding the azabicyclononane (cyclic amine) to the solution obtained above and stirring the solution at room temperature for 1 to 24 hours.

The 5-bromo-6-carbamates of the invention can be prepared in the following manner.

Compound XIII of the invention of the formula

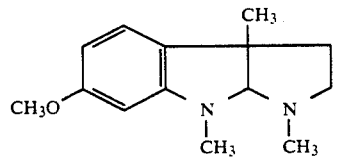

is reacted with an N-halosuccinimide, e.g., N-bromosuccinimide, N-chlorosuccinimide, a halogenating agent, of the formula

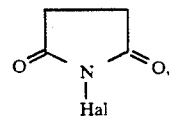

where Hal is halogen, to afford compound XV of the invention of the formula

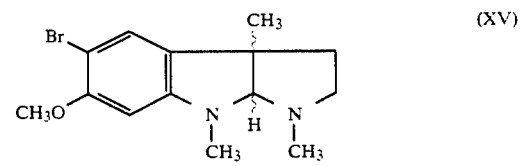

This reaction typically takes place in a loweralkanol solvent, e.g., methanol, ethanol, etc., in the presence of a catalyst, e.g., hydrogen bromide, hydrogen chloride, etc., at low temperature for 0.5 to 24 hours.

Compound XV is reacted with boron tribromide, a dealkylating agent, in a hydrocarbon or halohydrocarbon solvent, e.g., dichloromethane, hexane, etc., at a temperature of about 0° C. to 50° C. for 1 to 24 hours to afford Compound XVI of the invention of the formula

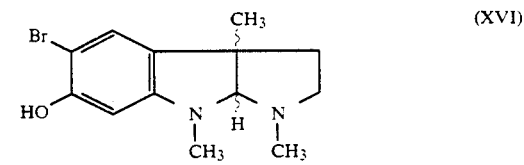

Compound XVI can subsequently react with DBU and an isocyanate of the formula $R_1$—N=C=O, where $R_1$ is as previously defined, to afford Compound XVII of the invention of the formula

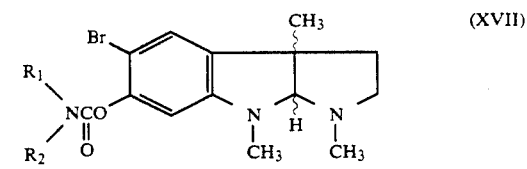

This reaction typically takes place in an inert solvent, i.e., benzene, etc., at ambient temperature for 0.5 to 24 hours.

The 4-phenol precursor of the 4-carbamate series can be prepared utilizing most of the synthetic scheme disclosed in Julian et al. In the Friedel-Crafts cyclization step (VII) to (VIII), we have discovered that there is a byproduct formed having formula (VIIIa) which serves as the precursor to the 4-phenol of the 4-carbamate series.

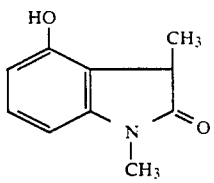

Subsequently, in place of the reaction step converting the cyanoalkyl derivative to the aminoalkyl derivative, the cyanoalkyl derivative, compound XVIII, of the invention of the formula

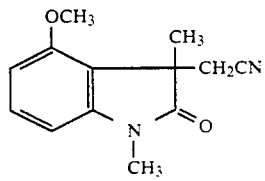

may be reacted with a metal hydride, e.g. lithium aluminum hydride, a reducing agent, to afford compound XIX of the invention of the formula

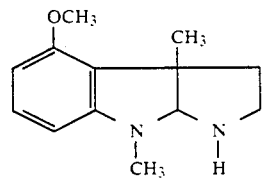

This reaction typically takes place in a suitable solvent, e.g., tetrahydrofuran at a temperature of 0° C. to 50° C. for 1 to 24 hours (or to reflux).

Compound XIX can be reacted with formaldehyde and sodium borohydride to afford Compound XX of the invention of the formula

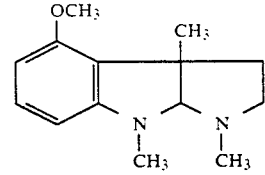

This reaction is typically conducted in a loweralkanol solvent, e.g. methanol, ethanol, in the presence of a base, e.g. triethylamine, at a temperature of 0° C. to 50° C. for 1 to 24 hours.

Compound XX is then reacted with aluminum chloride or boron tribromide to afford compound XXI of the invention of the formula

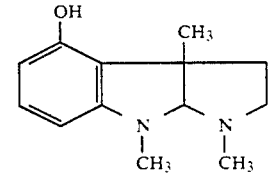

the 4-phenol immediate precursor of the 4-carbamoyl target compounds of this invention.

Compound XXI is reacted in the same manner as the 6-phenol precursor, i.e., with DBU in degassed benzene and then an isocyanate of the formula $R_1-N=C=O$ to afford Compound III of the invention.

The compounds of formula I of the present invention are useful in the treatment of various memory dysfunctions characterized by decreased cholinergic function, such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum cholinesterase) will give rise to fewer side effects and thus lower toxicity than physostigmine (an unspecific cholinesterase inhibitor). We have determined in vitro inhibition of acetylcholinesterase activity in rat striatum according to the method described below. Results of some of the compounds of this invention as well as those of physostigmine are presented in Table 1.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents 1. 005M Phosphate buffer, pH 7.2
   (a) 6.85 g $NaH_2PO_4.H_2O/100$ ml distilled $H_2O$
   (b) 13.40 g $Na_2HPO_4.7H_2O/100$ ml distilled $H_2O$
   (c) add (a) to (b) until pH reaches 7.2
   (d) dilute 1:10

2. Chromogen-substrate buffer
   (a) 9.9 mg 5,5-dithiobisnitrobenzoic acid (DTNB) (0.25 mM)
   (b) 99 mg s-acetylthiocholine chloride (5 mM)
   (c) q.s. to 100 ml with 0.05M phosphate buffer, pH 7.2 (reagent 1)

3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine $IC_{50}$ determinations the Abbott Bichromatic Analyzer, ABA-100, is used to determine acetylcholinesterase activity.

| Instrument settings |
| --- |
| Filter: 450-415 |
| Incubation temperature: 30° C. |
| Decimal point: 0000 |
| Analysis time: 5 minutes |
| Carousel Revolution: 3 |
| Reaction direction |
| : down |
| : endpoint |
| Syringe plate: 1:101 dilution |

Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with a Gilford 250 spectrophotometer. This method is used for more accurate kinetic measurements.

| Instrument settings | |
| --- | --- |
| Lamp: | visible |
| Filter: | no filter |
| Wavelength: | 412 nm |
| Slit width: | 0.2 mm |
| Selection: | small aperture |
| Calibrated absorbance: | 1.0 unit full scale |
| Chart speed: | 0.5 cm/min. |

| Reagents are added to the reference and sample side of a split curvette as follows: | |
| --- | --- |
| Reference | Sample |
| 0.8 ml 0.05M phosphate buffer | 0.8 ml 0.05M phosphate buffer |
| 0.8 ml Chromogen-substrate buffer | 0.8 ml Chromogen-substrate buffer |
| | 10 microliter enzyme (tissue homogenate) |

The unhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula $$\text{rate (moles/liter/min)} = \text{slope}/(1.36 \times 10^4)$$

Inhibition of Brain Acetycholinesterase Activity

TABLE 1

| Compound | Inhibitory Concentration ($10^{-6}$M) |
| --- | --- |
| cis-($\pm$)-1,2,3,3a,8,8a-Hexahydro-1,3a,8-trimethylpyrrolo[2,3-b]-indol-6-yl methylcarbamate | 0.23 |
| cis-($\pm$)-1,2,3,3a,8,8a-Hexahydro-1,3a,8-trimethylpyrrolo[2,3-b]-indol-6-yl cyclohexylcarbamate | 5.50 |
| cis-($\pm$)-5-Bromo-1,2,3,3a,8,8a-hexahydro-1,3a,8-trimethylpyrrolo[2,3-b]indol-6-yl methylcarbamate | 0.013 |
| cis-($\pm$)-1,2,3,3a,8,8a-Hexahydro-1,3a,8-trimethylpyrrolo[2.3-b]-indol-4-yl methylcarbamate | 0.06 |
| cis-($\pm$)-1,2,3,3a,8,8a-Hexahydro-1,3a,8-trimethylpyrrolo[2,3-b]indol-4-yl cyclohexylcarbamate | 0.55 |
| Physostigmine (namely, (3aS-cis)-1,2,3,3a,8,8a-hexahydro-1,3a,8-trimethylpyrrolo[2,3-b]indol-5-yl methylcarbamate) | 0.034 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, salicyclic, maleic, fumaric and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such compositions is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragecanth or gelatin; an excipient such as starch or lactose, a disintegrating agent such as alginic acid, Primogel ®, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of the invention include those listed below as well as the 3aS-cis and 3aR-cis isomers thereof and racemic mixtures of the 3aS-cis and 3aR-cis isomers.

cis-($\pm$)-5-chloro-1,2,3,3a,8,8a-hexahydro-1,3a,8-trimethylpyrrolo[2,3-b]indol-6-yl methylcarbamate;
(3aS-cis)-5-bromo-1,2,3,3a,8,8a-hexahydro-1,3a,8-trimethylpyrrolo[2,3-b]indol-6-yl methylcarbamate;
(3aS-cis)-1,2,3,3a,8,8a-hexahydro-1,3a,8-trimethylpyrrolo[2,3-b]indol-6-yl methylcarbamate;
(3aR-cis)-1,2,3,3a,8,8a-hexahydro-1,3a8-trimethylpyrrolo[2,3-b]indol-6-yl methylcarbamate;
(3aS-cis)-1,2,3,3a,8,8a-hexahydro-1,3a,8-trimethylpyrrolo[2,3-b]indol-4-yl methylcarbamate;
(3aR-cis)-1,2,3,3a,8,8a-hexahydro-1,3a,8-trimethylpyrrolo[2,3-b]indol-4-yl methylcarbamate;
cis-($\pm$)-5-bromo-1,2,3,3a8,8a-hexahydro-1,3a,8-trimethylpyrrolo[2,3-b]indol-4-yl methylcarbamate;
cis-($\pm$)-1,2,3,3a,8,8a-hexahydro-1,3a,8-trimethylpyrrolo[2,3-b]indol-6-yl benzylcarbamate;
cis-($\pm$)-1,2,3,3a,8,8a-hexahydro-1,3a,8-trimethylpyrrolo[2,3-b]indol-6-yl n-heptylcarbamate;
cis-($\pm$)-1,2,3,3a,8,8a-hexahydro-1,3a,8-trimethylpyrrolo[2,3-b]indol-6-yl 3-chlorophenylcarbamate;
cis-($\pm$)-1,2,3,3a,8,8a-hexahydro-1,3a,8-trimethylpyrrolo[2,3-b]indol-4-yl n-heptylcarbamate.

EXAMPLE 1

2-Bromo-N-(3-methoxyphenyl)-N-methyl-propanamide

A solution of N-methyl-m-ansidine (265 g), triethylamine (269 ml) and toluene (550 ml) was stirred at 0° C. as 2-bromopropionyl bromide (202.6 ml) was added dropwise. The mixture was mechanically stirred overnight at room temperature. Water was added to the reaction and the aqueous layer was collected and extracted with ethyl acetate. All organic phases were combined, washed with 2N HCl, and dried (Na$_2$SO$_4$). The solvent was evaporated to yield an oil which was purified using Kugelrohr distillation. The distillate was dissolved in isopropyl ether. The solid product, 2-Bromo-N-(3-methoxyphenyl)-N-methyl-propanamide, m.p. 55°-56° C., crystallized from this solution.

Analysis: Calculated for C$_{11}$H$_{14}$BrNO$_2$: 48.55% C; 5.19% H; 5.15% N. Found: 48.52% C; 5.22% H; 5.10% N.

EXAMPLE 2

1,3-Dihydro-6-hydroxy-1,3-dimethyl-2H-indol-2-one

To a 3-neck 1-liter round bottom flask equipped with a mechanical stirrer, addition funnel and condenser and purged continuously with nitrogen, was added anhydrous AlCl$_3$ (112 g), followed by 160 ml of 1,2-dichlorobenzene. The system was heated in an oil bath preset at 145° C. When the internal temperature reached $\approx$130° C., 2-bromo-N-(3-methoxyphenyl)-N-methylpropanamide (65.5 g), was added dropwise over a period of 15 minutes. After complete addition, the addition funnel was rinsed with 1,2-dichlorobenzene and added to the hot reaction mixture. After 2 hours at 145° C., the mixture was cooled to room temperature and then quenched into a stirred mixture containing 450 ml of concentrated HCl and 1.5 kg of ice. The reaction flask was rinsed with 500 ml of methylene chloride and added to the mixture which was then stirred for an additional 10 minutes. The mixture was filtered through a pad of Celite which was subsequently washed well with dichloromethane (DCM hereafter). The filtrate was poured into a separatory funnel. The organic phase was collected and dried over Na$_2$SO$_4$. The solvent was evaporated and the residual oil was purified by silica column chromatography (1% MeOH/DCM). This yielded a crude solid (28 g) which was recrystallized from methanol/ether to give 4.75 g of a powder, 1,3-dihydro-6-hydroxy-1,3-dimethyl-2H-indol-2-one, m.p. 176°-177° C. A second crop of product (19.6 g) was obtained from a recrystallization of the mother liquor solid bringing the total yield of the reaction to 24.35 g.

Analysis: Calculated for C$_{10}$H$_{11}$NO$_2$: 67.77% C; 6.27% H; 7.91% N. Found: 67.56% C; 6.24% H; 7.87% N.

EXAMPLE 3

1,3-Dihydro-6-methoxy-1,3-dimethyl-2H-indol-2-one

A slurry of 1,3-dihydro-6-hydroxy-1,3-dimethyl-2H-indol-2-one (56.6 g), milled potassium carbonate (65.9 g) and HPLC grade acetone (420 ml) was mechanically stirred at room temperature as dimethylsulfate (44.1 g) was added dropwise. The addition funnel was replaced with a condenser and the slurry was refluxed for 5 hours. The K$_2$CO$_3$ was filtered off and washed well with acetone. Acetone was evaporated and the residue was purified by Kugelrohr distillation to yield 37.2 g of an oil. The oil was dissolved in 75 ml of ether and placed in the refrigerator where, upon standing overnight, it solidified yielding 31.3 g of 1,3-dihydro-6-methoxy-1,3-dimethyl-2H-indol-2-one, m.p. 44°-46° C.

Analysis: Calculated for C$_{11}$H$_{13}$NO$_2$: 69.09% C; 6.85% H; 7.32% N. Found: 68.91% C; 6.71% H; 7.26% N.

EXAMPLE 4

3-Cyanomethyl-1,3-dihydro-6-methoxy-1,3-dimethyl-2H-indol-2-one 1,3-Dihydro-6-methoxy-1,3-dimethyl-2H-indol-2-one (16.4 g) and iodoacetonitrile (6.7 ml) were dissolved in dry ethanol (125 ml) and stirred while sodium ethoxide (5.8 g, 32 ml of a 21% by wt solution in tetrahydrofuran), was added dropwise. After the addition was complete, the mixture was refluxed for 3 hours. The ethanol was removed under reduced pressure and the residue was partitioned between ether and water. The ether layer was dried over $Na_2SO_4$ and concentrated to a residue which was purified by Prep 500 chromatography (DCM) to yield 13.2 g of the product as an oil. Trituration with ether yielded 10.4 g of a solid, 3-cyanomethyl-1,3-dihydro-6-methoxy-1,3-dimethyl-2H-indol-2-one, m.p. 107°–109° C.

Analysis: Calculated for $C_{13}H_{14}N_2O$: 67.81% C; 6.13% H; 12.17% N. Found: 67.75% C; 6.03% H; 12.13% N.

EXAMPLE 5

3-(2-aminoethyl)-1,3-dihydro-6-methoxy-1,3-dimethyl-2H-indol-2-one salicylate hemihydrate 3-(Cyanomethyl)-1,3-dihydro-6-methoxy-1,3-dimethyl-2H-indol-2-one (3 g) was dissolved in methanol (35 ml) and concentrated HCl (4.4 ml). This solution was combined with 10% $PtO_2$ (0.1 g) and hydrogenated under 50 psi for 2 hours. The methanol was removed under reduced pressure and the residue was diluted with 35 ml of ice cold water and 2.5 ml of 50% NaOH. The product was extracted with $CH_2Cl_2$, dried with $MgSO_4$ and evaporated to an oil. This oil was purified by Prep 500 chromatography (10% MeOH/DCM) to yield 2.5 g of an oil. The salicylate was precipitated from an ether solution to give 3.3 g of product 3-(2-aminoethyl)-1,3-dihydro-6-methoxy-1,3-dimethyl-2H-indol-2-one salicylate hemihydrate, m.p. 160° C.

Analysis: Calculated for $C_{13}H_{18}N_2O_2 \cdot C_7H_6O_3 \cdot 0.5H_2O$: 62.97% C; 6.62% H; 7.25% N. Found: 63.22% C; 6.56% H; 7.30% N.

EXAMPLE 6 cis-(±)-1,2,3,3a,8,8a-Hexahydro-6-methoxy-3a,8-dimethylpyrrolo[2,3-b]indole fumarate 3-(2-Aminoethyl)-1,3-dihydro-6-methoxy-1,3-dimethyl-2H-indol-2-one (52 g) was dissolved in ethanol (1.5 l) and heated to reflux under nitrogen. Sodium metal (≈75 g) was added in small chunks over ½ hour. After all the sodium had reacted, the mixture was refluxed for an additional 15 minutes. Ethanol was removed under reduced pressure. The residue was diluted with $H_2O$ (1.5 l) and extracted with $CH_2Cl_2$ (2.5 l). The $CH_2Cl_2$ solution was dried and evaporated. The residue was purified by Prep 500 chromatography (3% MeOH/DCM) to give 17.7 g of an oil. The fumarate was precipitated from MeOH/ether to give the solid, cis-(±)-1,2,3,3a,8,8a-hexahydro-6-methoxy-3a,8-dimethylpyrrolo[2,3-b]indole fumarate, m.p. 176°–177° C.

Analysis: Calculated for $C_{13}H_{18}N_2O \cdot C_4H_4O_4$: 61.07% C; 6.63% H; 8.38% N. Found: 60.84% C; 6.71% H; 8.26% N.

EXAMPLE 7 cis-(±)-1,2,3,3a,8,8a-Hexahydro-6-methoxy-1,3a,8-trimethylpyrrolo[2,3-b]indole fumarate cis-(±)-1,2,3,3a,8,8a-Hexahydro-6-methoxy-3a,8-dimethylpyrrolo[2,3-b]indole (12 g) was dissolved in methanol (250 ml) with triethylamine (20 ml) and 37% aqueous formaldehyde (28.6 ml). The mixture was stirred at room temperature for ¼ hour and then cooled to 0° C. Sodium borohydride (8.6 g) was added slowly in portions. After one hour, the mixture was concentrated on the rotary evaporator. Hydrochloric acid (2N) was added in sufficient amount to dissolve the residue. This acidic solution was extracted again with ether, basified with saturated aqueous $Na_2CO_3$, and extracted with ether. The residue was purified using Prep 500 chromatography (5% MeOH/DCM) to yield 9.8 g of an oil, cis-(±)-1,2,3,3a,8,8a-hexahydro-6-methoxy-1,3a,8-trimethylpyrrolo[2,3-b]indole. The fumarate, mp 138°–139° C., was precipitated from a methanol/ether solution.

Analysis Calculated for $C_{14}H_{20}N_2O \cdot C_4H_4O_4$: 62.05% C; 6.94% H; 8.04% N. Found: 62.29% C; 7.10% H; 8.07% N.

EXAMPLE 8 cis-(±)-1,2,3,3a,8,8a-Hexahydro-1,3a,8-trimethylpyrrolo[2,3-b]indol-6-ol fumarate cis-(±)-1,2,3,3a,8,8a-Hexahydro-6-methoxy-1,3a,8-trimethylpyrrolo[2,3-b]indole (5 g) was dissolved in DCM (50 ml). This solution was added to a solution of $BBr_3$ (32.4 ml, 1M in DCM) which was stirred at 0° C. under nitrogen. The mixture was stirred for 1 hour and then quenched with 150 ml of a saturated $NaHCO_3$ solution added dropwise. An additional 300 ml of saturated $NaHCO_3$ was added and the mixture was extracted with 4:1 $CHCl_3$-isopropyl alcohol ("IPA" hereafter). The organic extracts were dried ($Na_2SO_4$), filtered and evaporated to yield a solid. The solid was dissolved in $CHCl_3$ and a small amount of silica gel was added. The slurry was stirred at room temperature under $N_2$ for 10 minutes. The mixture was filtered and the filtrate was decolorized with activated charcoal and evaporated to 2.3 g of an oil. The fumarate (400 mg) was precipitated from MeOH/ether yielding a solid, cis-(±)-1,2,3,3a,8,8a-hexahydro-1,3a,8-trimethylpyrrolo[2,3-b]indol-6-ol fumarate, m.p. 193°–194° C.

Analysis: Calculated for $C_{13}H_{18}N_2O \cdot C_4H_4O_4$: 61.07% C; 6.63% H; 8.38% N. Found: 60.78% C; 6.85% H; 8.17% N.

EXAMPLE 9 cis-(±)-1,2,3,3a,8,8a-Hexahydro-1,3a,8-trimethylpyrrolo[2,3-b]indol-6-yl methylcarbamate salicylate cis-(±)-1,2,3,3a,8,8a-Hexahydro-1,3a,8-trimethylpyrrolo[2,3-b]indol-6-ol (1.5 g) was added to degassed benzene (150 ml). After 5 minutes of stirring at room temperature, 1,8-diazabicyclo[5.4.0]undec-7-ene (hereafter "DBU") (0.1 ml) was added to the mixture. Methyl isocyanate (0.9 ml) was subsequently added very slowly (in several portions) over a period of 1.5 hours. The benzene was evaporated and the residue was purified using Prep 500 chromatography (5% MeOH/DCM) to yield 1.15 g of an oil. The salicylate (920 mg), m.p. 148°–149° C., was precipitated from dry diethyl ether.

Analysis: Calculated for $C_{15}H_{21}N_3O_2 \cdot C_7H_6O_5$: 63.91% C; 6.58% H; 10.16% N. Found: 64.31% C; 6.43% H; 10.20% N.

EXAMPLE 10

(±)-(3aR*,8aS*)-1,2,3,3a,8,8a-Hexahydro-1,3a,8-trimethylpyrrolo[2,3-b]indol-6-yl (R)-(α-methylbenzyl)carbamate salicylate cis-(±)-1,2,3,3a,8,8a-Hexahydro-1,3a,8-trimethylpyrrolo[2,3-b]indol-6-ol (1 g) was added to degassed benzene (150 ml). After 5 minutes of stirring at room temperature, DBU (0.1 ml) was added to the mixture. (R)-(±)-α-methylbenzyl isocyanate (0.66 ml) was added slowly dropwise and the reaction was complete in ½ hour. The benzene was evaporated and the residue was purified using Prep 500 chromatography (5% MeOH/DCM) to yield 0.68 g of an oil. The product, (±)-(3aR*,8aS*)-1,2,3,3a,8,8a-hexahydro-1,3a,8-trimethylpyrrolo[2,3-b]indol-6-yl (R)-(α-methylbenzyl)carbamate salicylate, m.p. 119°–120° C. (0.72 g) was precipitated from dry diethyl ether.

Analysis: Calculated for $C_{22}H_{27}N_3O_2 \cdot C_7H_6O_3$ 69.17% C; 6.61% H; 8.34% N. Found: 69.12% C; 6.31% H; 8.36% N.

EXAMPLE 11

(±)-(3aR*,8aS*)-1,2,3,3a,8,8a-Hexahydro-1,3a,8-trimethylpyrrolo [2,3-b]indol-6-yl (S)-(α-methylbenzyl)carbamate salicylate cis-(±)-1,2,3,3a,8,8a-Hexahydro-1,3a,8-trimethylpyrrolo[2,3-b]indol-6-ol(1 g) was added to degassed benzene (150 ml). After 5 minutes of stirring at room temperature, DBU (0.1 ml) was added to the mixture. (S)-(−)-α-methylbenzyl isocyanate (1 ml) was added slowly dropwise. The reaction was complete in ½ hour. The benzene was evaporated and the residue was purified using Prep 500 chromatography (5% MeOH/DCM) to yield 0.79 g of an oil. This product was combined with another lot of identically prepared material, which was found to be pure by thin layer analysis. The salicylate of the combined product was precipitated from dry diethyl ether giving a salt, (±)-(3aR*,8aS*)-1,2,3,3a,8,8a-hexahydro-1,3a,8-trimethylpyrrolo[2,3-b]indol-6-yl (S)-(α-methylbenzyl)carbamate salicylate, m.p. 118°–119° C.

Analysis: Calculated for $C_{22}H_{27}N_3O_2 \cdot C_7H_6O_3$: 69.17% C; 6.61% H; 8.35% N. Found: 69.17% C; 6.65% H; 8.29% N.

EXAMPLE 12 cis-(±)-1,2,3,3a,8,8a-Hexahydro-1,3a,8-trimethylpyrrolo[2,3-b]indol-6-yl cyclohexyl carbamate salicylate cis-(±)-1,2,3,3a,8,8a-Hexahydro-1,3a,8-trimethylpyrrolo[2,3-b]indol-6-ol (1 g) was added to degassed benzene (150 ml). After 5 minutes of stirring at room temperature, DBU (0.1 ml) was added to the mixture. Cyclohexyl isocyanate (0.76 ml), was added slowly dropwise and the reaction was complete in ½ hour. The benzene was evaporated and the residue was purified using Prep 500 chromatography (5% MeOH/DCM) to yield 0.90 g of an oil. The product was combined with another lot of identically prepared material, which was found to be pure by thin layer analysis. The salicylate of the combined product was precipitated from dry diethyl ether and recrystallized from EtOAc/hexane to yield the product, cis-(±)-1,2,3,3a,8,8a-hexahydro-1,3a,8-trimethylpyrrolo[2,3-b]indol-6-yl cyclohexyl carbamate salicylate, m.p. 155°–156° C.

Analysis: Calculated for $C_{20}H_{29}N_3O_2 \cdot C_7H_6O_3$: 67.34% C; 7.33% H; 8.73% N. Found: 66.97% C; 7.25% H; 8.60% N.

EXAMPLE 13 cis-(±)-1,2,3,3a,8,8a-Hexahydro-1,3a,8-trimethylpyrrolo[2,3-b]indol-6-yl 3-[3-azabicyclo[3.2.2]nonane]carbamate fumarate cis-(±)-1,2,3,3a,8,8a-Hexahydro-1,3a,8-trimethylpyrrolo[2,3-b]indol-6-ol (2 g) was dissolved in dry degassed dichloromethane. 1,1′Carbonyldiimidazole (1.64 g) was added in one portion. The mixture was stirred for ½ hour at room temperature under $N_2$. 3-Azabicyclo[3.2.2]nonane (1.7 g) was added and the mixture was stirred at room temperature overnight under nitrogen. The solution was evaporated and the residue was purified using Prep 500 chromatography (3% MeOH/DCM) to yield 1.25 g of the product as an oil. The fumarate was precipitated from MeOH/ether to yield 0.82 g of a solid. This material was combined with 0.6 g of product from another lot of identically prepared material, which was found to be pure by thin layer analysis. The combined material was recrystallized from methanol to yield the product, cis-(±)-1,2,3,3a,8,8a-hexahydro-1,3a,8-trimethylpyrrolo[2,3-b]indol-6-yl 3-[3-azabicyclo[3.2.2]nonane]carbamate fumarate, m.p. 153°–154° C.

Analysis: Calculated for $C_{22}H_{31}N_3O_2 \cdot C_4H_4O_4$: 64.31% C; 7.27% H; 8.65% N. Found: 64.35% C; 7.18% H; 8.59% N.

EXAMPLE 14 cis-(±)-1,2,3,3a,8,8a-Hexahydro-1,3a,8-trimethylpyrrolo[2,3-b]indol-6-yl phenyl carbamate fumarate cis-(±)-1,2,3,3a,8,8a-Hexahydro-1,3a,8-trimethylpyrrolo[2,3-b]indol-6-ol (3 g) was dissolved in THF (200 ml). DBU (1 ml) was added followed by phenyl isocyanate (2.1 ml). The mixture was stirred at room temperature under nitrogen overnight. The solvent was removed under reduced pressure and the residue was purified using Prep 500 chromatography (3% MeOH/DCM) to yield 1.3 g of an oil. This oil was dissolved in a small amount of methanol. Fumaric acid (0.49 g) was also dissolved in methanol and was added to the free base in solution. Upon addition of ethyl ether, the product crystallized out of solution to yield 1.2 g of solid, cis-(±)-1,2,3,3a,8,8a-hexahydro-1,3a,8-trimethylpyrrolo[2,3-b]indol-6-yl phenyl carbamate fumarate, m.p. 180° C.

Analysis: Calculated for $C_{20}H_{23}N_3O_2 \cdot C_4H_4O_4$: 63.57% C; 6.00% H; 9.27% N. Found: 63.14% C; 6.11% H; 9.13% N.

EXAMPLE 15 cis-(±)-5-Bromo-1,2,3,3a,8,8a-hexahydro-6-methoxy-1,3a,8-trimethylpyrrolo[2,3-b]indole fumarate cis-(±)-1,2,3,3a,8,8a-Hexahydro-6-methoxy-1,3a,8-trimethylpyrrolo[2,3-b]indole (21.2 g) dissolved in methanol (200 ml) and 48% HBr (0.5 ml) was treated with N-bromosuccinimide (17.9 g) in several portions at 0° C. After one hour at room temperature, the solution was evaporated and the residue was purified by Prep 500 chromatography (3% MeOH/DCM) to yield 13 g of an oil. The oil (2 g) was dissolved in methanol and a concentrated solution of fumaric acid (0.82 g) in methanol was added dropwise. The product salt (1.8 g) precipitated out of solution upon addition of ethyl ether. Recrystallization from methanol yielded 1.4 g of the pure product, cis-($\pm$)-5-bromo-1,2,3,3a,8,8a-hexahydro-6-methoxy-1,3a,8-trimethylpyrrolo[2,3-b]indole fumarate, m.p. 177°–178° C.

Analysis: Calculated for $C_{14}H_{19}BrN_2O \cdot C_4H_4O_4$: 50.60% C; 5.43% H; 6.56% N. Found: 50.69% C; 5.49% H; 6.50% N.

EXAMPLE 15a cis-($\pm$)-5-Bromo-1,2,3,3a,8,8a-hexahydro-1,3a,8-trimethylpyrrolo[2,3-b]indol-6-ol cis-($\pm$)-5-Bromo-1,2,3,3a,8,8a-hexahydro-6-methoxy-1,3a,8-trimethylpyrrolo[2,3-b]indole (11 g) was dissolved in dry DCM (200 ml) and added dropwise at 0° C. to a stirred solution of BBr$_3$ in DCM (300 ml). The mixture was warmed to room temperature and stirred overnight under nitrogen. The mixture was quenched with aq. Na$_2$CO$_3$ and aq. NaHCO$_3$ until basic at 0° C. The organic layer was dried and evaporated to a foam (10 g). The IR, NMR and Mass Spectra confirmed the purity and identity of this product.

EXAMPLE 16 cis-($\pm$)-5-Bromo-1,2,3,3a,8,8a-hexahydro-1,3a,8-trimethylpyrrolo[2,3-b]indol-6-yl methyl carbamate sesquifumarate cis-($\pm$)-5-Bromo-1,2,3,3a,8,8a-hexahydro-1,3a,8-trimethylpyrrolo[2,3-b]indol-6-ol (2.4 g) was added to a solution of DBU (1.3 ml) in benzene (200 ml). Methyl isocyanate (0.71 ml) was subsequently added dropwise. The mixture was stirred overnight at room temperature under N$_2$. The solution was evaporated and the residue was purified by Prep 500 chromatography (1% TEA/5% MeOH/94% DCM) to yield 1.1 g of an oil. Fumaric acid (0.36 g) in methanol was added to the oil which was also dissolved in methanol. Upon addition of ethyl ether, the product salt (0.860 g), precipitated out of solution. This product was combined with 600 mg of another lot of identically prepared material, which was found to be pure by thin layer analysis. This combined product was recrystallized from methanol to yield 900 mg product, cis-($\pm$)-5-bromo-1,2,3,3a,8,8a-hexahydro-1,3a,8-trimethylpyrrolo[2,3-b]indol-6-yl methyl carbamate sesquifumarate, m.p. 180° C.

Analysis: Calculated for $C_{15}H_{20}BrN_3O_2 \cdot 1.5C_4H_4O_4$: 47.73% C; 4.97% H; 7.95% N. Found: 47.72% C; 4.99% H; 7.91% N.

EXAMPLE 17

1,3-Dihydro-4-hydroxy-1,3-dimethyl-2H-indol-2-one

To a 3-neck 1-liter round bottom flask equipped with a mechanical stirrer, addition funnel and condenser and purged with nitrogen, was added anhydrous AlCl$_3$ (256.5 g) followed by 380 ml of 1,2-dichlorobenzene. The system was heated in an oil bath preset at 145° C. When the internal temperature reached approximately 130° C., 2-bromo-N-(3-methoxyphenyl)-N-methylpropanamide (150 g) was added dropwise. After complete addition funnel was rinsed with 1,2-dichlorobenzene and added to the hot reaction mixture. After 2 hours at 145° C., the mixture was cooled to room temperature and then quenched into a stirred mixture containing 1 liter of concentrated HCl and 3 kg of ice. The reaction flask was rinsed with a few milliliters of CH$_2$Cl$_2$ and added to the mixture which was stirred for an additional ten minutes. The mixture was filtered through a pad of celite and the filtrate was poured into a separatory funnel. The organic phase was collected and dried over MgSO$_4$. The solvent was evaporated and the residual oil was combined with another lot of identically prepared material which was found to be pure by thin layer analysis. The combined reaction mixtures were purified by SiO$_2$ column chromatography (20% ethyl acetate/hexane). The product, 1,3-dihydro-4-hydroxy-1,3-dimethyl-2H-indol-2-one monohydrate, (27.5 g) m.p. 150°–151° C., crystallized directly out of the eluent.

Analysis: Calculated for $C_{10}H_{11}NO_2 \cdot H_2O$: 61.53% C; 6.71% H; 7.17% N. Found: 61.83% C; 6.77% H; 7.18% N.

EXAMPLE 18

1,3-Dihydro-4-methoxy-1,3-dimethyl-2H-indol-2-one

A slurry of 1,3-dihydro-4-hydroxy-1,3-dimethyl-2H-indol-2-one (50 g), milled potassium carbonate (60.1 g) and HPLC grade acetone (400 ml) was mechanically stirred at room temperature as dimethylsulfate (41.4 ml) was added dropwise. The addition funnel was replaced with a condenser and the slurry was refluxed for 18 hours. The K$_2$CO$_3$ was filtered off and washed well with acetone. Acetone was evaporated and the residue was purified by column chromatography to yield 46.5 g of an oil. The oil was dissolved in ether and placed in the refrigerator where, upon standing overnight, the product crystallized, m.p. 73°–74° C.

Analysis: Calculated for $C_{11}H_{13}NO_2$: 69.09% C; 6.85% H; 7.32% N. Found: 68.99% C; 6.77% H; 7.34% N.

EXAMPLE 19

3-Cyanomethyl-1,3-dihydro-4-methoxy-1,3-dimethyl-2H-indol-2-one 1,3-Dihydro-4-methoxy-1,3-dimethyl-2H-indol-2-one (43 g) and iodoacetonitrile (17.5 ml) were dissolved in dry ethanol (325 ml) and stirred while sodium ethoxide (83.9 ml of a 21% solution in ethanol) was added dropwise. After the addition was complete, the mixture was stirred overnight under nitrogen. The ethanol was removed under reduced pressure and the residue was partitioned between ether and water. The ether layer was washed with 10% NaOH and dried over Na$_2$SO$_4$. The ether was removed and the residue was purified by column chromatography (15% EtOAc/hexane) to yield 41.2 g of the product, 3-cyanomethyl-1,3-dihydro-4-methoxy-1,3-dimethyl-2H-indol-2-one, as an oil, which solidified upon standing. Trituration with ether yielded a solid (15.0 g), m.p. 92°–93° C.

Analysis: Calculated for $C_{13}H_{14}N_2O_2$: 67.81% C; 6.13% H; 12.17% N. Found: 67.74% C; 6.15% H; 12.16% N.

EXAMPLE 20 cis-($\pm$)-1,2,3,3a,8,8a-Hexahydro-4-methoxy-3a,8-dimethylpyrrolo[2,3-b]indole fumarate 3-Cyanomethyl-1,3-dihydro-4-methoxy-1,3-dimethyl-2H-indol-2-one (15.0 g) was dissolved in tetrahydrofuran (750 ml) and stirred at 0° C. Lithium aluminum hydride (130.4 ml of 1M solution in THF) was added dropwise under N$_2$. The mixture was refluxed for ½ hour, cooled, and quenched with 5 ml H$_2$O, followed by 7.5 ml 10% NaOH and finally more H$_2$O (15 ml). The aluminum hydroxide salts were filtered off through a pad of Celite and washed well with THF. The filtrate was concentrated. Water (250 ml) was added and the aqueous solution was extracted with ether (1 L). The ether extract was dried with MgSO$_4$ and evaporated. The residue was purified using Prep 500 chromatography (5% MeOH/DCM) to yield 8.3 g of an oil. The fumarate was precipitated from methanol/ether to yield the salt, cis-($\pm$)-1,2,3,3a,8,8a-hexahydro-4-methoxy-3a,8-dimethylpyrrolo[2,3-b]indole fumarate, m.p. 132°–133° C.

Analysis: Calculated for C$_{13}$H$_{18}$N$_2$O.C$_4$H$_4$O$_4$: 61.07% C; 6.63% H; 8.38% N. Found: 61.10% C; 6.74% H; 8.30% N.

EXAMPLE 21 cis-($\pm$)-1,2,3,3a,8,8a-Hexahydro-4-methoxy-1,3a,8-trimethylpyrrolo[2,3-b]indole fumarate cis-($\pm$)-1,2,3,3a,8,8a-Hexahydro-4-methoxy-3a,8-dimethylpyrrolo[2,3-b]indole (2.1 g) was dissolved in methanol (50 ml). Triethylamine (3.3 ml) and 37% aqueous formaldehyde (5 ml) were added and the mixture was then stirred at room temperature for 1 hour. The solution was cooled to 0° C. and NaBH$_4$ (1.5 g) was added in portions. After 1 hour, the reaction was quenched with enough 2N HCl added dropwise to make the mixture slightly acidic. Methanol was removed under reduced pressure and saturated aqueous Na$_2$CO$_3$ was added to the residue. This aqueous solution was extracted with ether. The ether was evaporated and the residue was purified by Prep 500 chromatography to yield 2 g of an oil. The fumarate was precipitated from methanol/ether to yield the salt, cis-($\pm$)-1,2,3,3a,8,8a-hexahydro-4-methoxy-1,3a,8-trimethylpyrrolo [2,3-b]indole fumarate, m.p. 187°–188° C.

Analysis: Calculated for C$_{14}$H$_{20}$N$_2$O.C$_4$H$_4$O$_4$: 62.05% C; 6.94% H; 8.04% N. Found: 62.17% C; 6.96% H; 8.04% N.

EXAMPLE 22 cis-($\pm$)-1,2,3,3a,8,8a-Hexahydro-1,3a,8-trimethylpyrrolo [2,3-b]indol-4-ol fumarate cis-($\pm$)-1,2,3,3a,8,8a-Hexahydro-4-methoxy-1,3a,8-trimethylpyrrolo [2,3-b]indole (22.0 g) was dissolved in DCM (300 ml). This solution was added dropwise to a solution of boron tribromide (300 ml of a 1M solution) which was stirred at 0° C. under nitrogen. The mixture was stirred overnight under nitrogen at room temperature. The reaction mixture was then slowly poured into a stirring saturated solution of Na$_2$CO$_3$ (200 ml) at 0° C. Saturated NaHCO$_3$ was added slowly until the mixture became slightly alkaline which was then extracted with 4:1 CHCl$_3$/isopropyl alcohol. The organic extracts were dried (MgSO$_4$), filtered and evaporated to yield 20 g of a foam. Approximately 2 g of this material was chromatographed using Prep 500 chromatography (10% MeOH/DCM) to yield 1.2 g of an oil which was dissolved in methanol. Fumaric acid (0.7 g) was also dissolved in methanol and added to the free base. Ethyl ether was added slowly and 1.1 g of the product, cis-($\pm$)-1,2,3,3a,8,8a-hexahydro-1,3a,8-trimethylpyrrolo [2,3-b]indol-4-ol fumarate, m.p. 196°–198° C., crystallized out of solution.

Analysis: Calculated for C$_{13}$H$_{18}$N$_2$O.C$_4$H$_4$O$_4$: 61.05% C; 6.64% H; 8.38% N. Found: 61.00% C; 6.75% H; 8.22% N.

EXAMPLE 23 cis-($\pm$)-1,2,3,3a,8,8a-Hexahydro-1,3a,8-trimethylpyrrolo[2,3-b]indol-4-yl methylcarbamate fumarate cis-($\pm$)-1,2,3,3a,8,8a-Hexahydro-1,3a,8-trimethylpyrrolo[2,3-b]indol-4-ol (1.5 g) was added to a solution of DBU (0.1 g) in benzene (100 ml) followed by the addition of methyl isocyanate (0.81 ml). The mixture was stirred overnight under nitrogen. The solution was evaporated and the residue was purified by Prep 500 chromatography (3% MeOH/DCM) to yield 0.65 g of an oil. The oil was dissolved in methanol and a concentrated solution of fumaric acid (0.30 g) in methanol was added dropwise. Upon addition of ethyl ether, 560 mg of pure product, cis-($\pm$)-1,2,3,3a,8,8a-hexahydro-1,3a,8-trimethylpyrrolo[2,3-b]indol-4-yl methylcarbamate fumarate, m.p. 175° C., precipitated out of solution.

Analysis: Calculated for C$_{15}$H$_{21}$N$_3$O$_2$.C$_4$H$_4$O$_4$: 58.30% C; 6.44% H; 10.74% N. Found: 58.47% C; 6.50% H; 10.73% N.

EXAMPLE 24 cis-($\pm$)-1,2,3,3a,8,8a-Hexahydro-1,3a,8-trimethylpyrrolo[2,3-b]-indol-4-yl cyclohexyl carbamate fumarate cis-($\pm$)-1,2,3,3a,8,8a-Hexahydro-1,3a,8-trimethylpyrrolo[2,3-b]indol-4-ol (2.1 g) was added to degassed benzene (500 ml). DBU (1.6 ml) was added to the mixture followed by cyclohexyl isocyanate (1.8 ml). The reaction was stirred at room temperature overnight under nitrogen. The benzene was evaporated and the residue was purified using Prep 500 chromatography (5% MeOH/DCM) to yield 2.3 g of a foam. Fumaric acid (0.78 g) dissolved in isopropyl alcohol was added to this foam which was also dissolved in isopropyl alcohol. The fumarate precipitated from solution upon addition of diethylether to yield 1.5 g of the salt, cis-($\pm$)-1,2,3,3a,8,8a-hexahydro-1,3a,8-trimethylpyrrolo[2,3-b]indol-4-yl, cyclohexyl carbamate fumarate, m.p. 179°–180° C.

Analysis: Calculated for C$_{20}$H$_{29}$N$_3$O$_2$.C$_4$H$_4$O$_4$: 62.73% C; 7.24% H; 9.14% N. Found: 62.78% C; 7.22% H; 9.07% N.

EXAMPLE 25

($\pm$)-(3aR*,8aS*)-1,2,3,3a,8,8a-Hexahydro-1,3a,8-trimethylpyrrolo[2,3-b]indol-4-yl (R)-($\alpha$-methylbenzyl)carbamate cis-($\pm$)-1,2,3,3a,8,8a-Hexahydro-1,3a,8-trimethylpyrrolo [2,3-b]indol-4-ol (2 g) was dissolved in degassed THF (200 ml). DBU (0.8 ml) was added to the mixture followed by R-(+)-$\alpha$-methylbenzyl isocyanate (2 g). The reaction was stirred at room temperature overnight under nitrogen. The solvent was evaporated under reduced pressure and the residue was purified using Prep 500 chromatography (4% MeOH/DCM) to yield 1.2 g of a solid. This material was combined with 600 mg of identically prepared material, which was found to be pure by thin layer analysis. The combined product was triturated with isopropyl ether and filtered to yield 1.8 g of ($\pm$)-(3aR*, 8aS*)-1,2,3,3a,8,8a-hexahydro-1,3a,8-trimethylpyrrolo [2,3-b]indol-4-yl (R)-($\alpha$-methylbenzyl)carbamate, m.p. 151°–155° C.

Analysis: Calculated for C$_{22}$H$_{27}$N$_3$O$_2$: 72.30% C; 7.45% H; 11.50% N. Found: 72.32% C; 7.58% H; 11.53% N.

We claim:

1. A compound of the formula

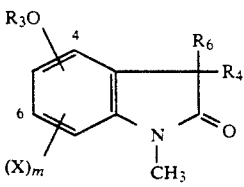

where $R_3$ is hydrogen or loweralkyl; $R_4$ is hydrogen, cyanomethyl or aminoethyl; $R_6$ is loweralkyl; m is 0, 1, or 2; each X is independently hydrogen, halogen, loweralkyl, nitro or amino or the pharmaceutically acceptable acid addition salts thereof.

2. The compound as defined in claim 1 where $R_3$ is hydrogen.

3. The compound as defined in claim 2 where $OR_3$ is at the 6-position of the indole ring.

4. The compound as defined in claim 2 which is 1,3-dihydro-6-hydroxy-1,3-dimethyl-2H-indol-2-one.

5. The compound as defined in claim 2 where $OR_3$ is at the 4-position of the indole ring.

6. The compound as defined in claim 5 which is 1,3-dihydro-4-hydroxy-1,3-dimethyl-2H-indol-2-one monohydrate.

7. The compound as defined in claim 1 where $R_3$ is loweralkyl.

8. The compound as defined in claim 7 where $OR_3$ is at the 6-position of the indole ring.

9. The compound as defined in claim 8 which is 1,3-dihydro-6-methoxy-1,3-dimethyl-2H-indol-2-one.

10. The compound as defined in claim 8 which is 3-cyanomethyl-1,3-dihydro-6-methoxy-1,3-dimethyl-2H-indol-2-one.

11. The compound as defined in claim 8 which is 3-(2-aminoethyl)-1,3-dihydro-6-methoxy-1,3-dimethyl-2H-indol-2-one salicylate hemihydrate.

12. The compound as defined in claim 7 where $OR_3$ is at the 4-position of the indole ring.

13. The compound as defined in claim 12 which is 1,3-dihydro-4-methoxy-1,3-dimethyl-2H-indol-2-one.

14. The compound as defined in claim 12 which is 3-cyanomethyl-1,3-dihydro-4-methoxy-1,3-dimethyl-2H-indol-2-one.

* * * * *